United States Patent
Smith et al.

[11] Patent Number: 6,142,998
[45] Date of Patent: Nov. 7, 2000

[54] BONE GRAFT DELIVERY SURGICAL INSTRUMENTS

[75] Inventors: Margaret E. Smith, White Plains; Michael J. Cusick, Suffern, both of N.Y.

[73] Assignee: Howmedica Osteonics Corp., Allendale, N.J.

[21] Appl. No.: 09/476,272

[22] Filed: Jan. 3, 2000

Related U.S. Application Data

[62] Division of application No. 08/988,095, Dec. 10, 1997, Pat. No. 6,045,555, which is a continuation of application No. 08/336,841, Nov. 9, 1994, Pat. No. 5,697,932.

[51] Int. Cl.[7] .......................... A61B 17/56; A61M 5/315
[52] U.S. Cl. ............................... 606/86; 606/95; 604/218
[58] Field of Search .................... 606/86, 92–95; 604/181, 218

[56] References Cited

U.S. PATENT DOCUMENTS

| Re. 32,488 | 9/1987 | Gustilo et al. | 623/23 |
|---|---|---|---|
| D. 272,648 | 2/1984 | Bolesky et al. | D24/28 |
| D. 273,806 | 5/1984 | Bolesky et al. | D24/28 |
| 2,537,070 | 1/1951 | Longfellow | 128/92 |
| 2,543,780 | 3/1951 | Hipps et al. | 128/83 |
| 2,621,145 | 12/1952 | Sano | 167/84 |
| 2,955,530 | 10/1960 | Nils | 100/289 |
| 3,048,522 | 8/1962 | Velley | 167/74.6 |
| 3,255,570 | 6/1966 | Weimer | 53/390 |
| 3,514,791 | 6/1970 | Sparks | 3/1 |
| 3,554,192 | 1/1971 | Isberner | 128/83 |
| 3,625,198 | 12/1971 | Sparks | 128/1 |

(List continued on next page.)

FOREIGN PATENT DOCUMENTS

| 0058744 | 9/1981 | European Pat. Off. . |
|---|---|---|
| 0106960 A1 | 8/1983 | European Pat. Off. . |
| 0143847 | 11/1983 | European Pat. Off. . |
| 0179626 | 10/1985 | European Pat. Off. . |
| 0218492 | 8/1986 | European Pat. Off. . |
| 0253526 | 6/1987 | European Pat. Off. . |
| 0331623 | 1/1989 | European Pat. Off. . |
| 0434604 | 11/1990 | European Pat. Off. . |
| 0457464 | 5/1991 | European Pat. Off. . |
| 0470393 A1 | 7/1991 | European Pat. Off. . |
| 2395011 | 6/1977 | France . |

(List continued on next page.)

OTHER PUBLICATIONS

St. Urban Gronert–Weigert Hip Joint Surface Replacement Instrumentation and Surgical Technique.

Howmedica, Inc. Orthopaedics Division CAD Hip System Instrumentation (1978).

Complications of Total Hip Arthroplasty, Drs. Rothman and Hozack, 1988, pp. 93–98; 110–123 and 156.

Histology of Cancellous Impaction Grafting In The Femur, Ling, Timperley & Linder vol. 75–B No. 5 Sep. 1993.

Impacted Cancellous Allografts And Cement For Revision Total Hip Arthroplasty, G.A., Gie et al., vol. 75–B, No. 1, Jan. 1993.

(List continued on next page.)

*Primary Examiner*—Paul J. Hirsch
*Assistant Examiner*—Michael B. Priddy
*Attorney, Agent, or Firm*—Lerner, David, Littenberg, Krumholz & Mentlik, LLP

[57] ABSTRACT

Surgical instruments comprise a hollow tube constructed to receive bone graft, and a plunger to be inserted into the hollow tube. The plunger is constructed and arranged with respect to the hollow tube so as to form a positive impression in the bone graft when the bone graft and the plunger are within the hollow tube. The plunger is further constructed and arranged so that when the hollow tube is moved in a direction away from a graft receiving area, the bone graft is delivered to the graft receiving area with the same positive impression that was formed within the hollow tube.

5 Claims, 9 Drawing Sheets

U.S. PATENT DOCUMENTS

| | | | |
|---|---|---|---|
| 3,740,769 | 6/1973 | Haboush | 128/92 |
| 3,782,373 | 1/1974 | Smythe | 128/92 EB |
| 3,793,650 | 2/1974 | Ling et al. | 128/92 |
| 3,829,904 | 8/1974 | Ling et al. | 128/92 |
| 3,846,846 | 11/1974 | Fischer | 128/92 |
| 3,874,003 | 4/1975 | Moser et al. | 128/92 |
| 3,896,505 | 7/1975 | Timmermans . | |
| 3,906,550 | 9/1975 | Rostoker et al. . | |
| 3,918,100 | 11/1975 | Shaw et al. . | |
| 3,965,490 | 6/1976 | Murray et al. . | |
| 3,986,212 | 10/1976 | Sauer . | |
| 4,004,581 | 1/1977 | Heimke et al. | 128/92 |
| 4,080,666 | 3/1978 | Fixel . | |
| 4,108,161 | 8/1978 | Samuels et al. | 128/1 R |
| 4,141,088 | 2/1979 | Treace et al. . | |
| 4,184,490 | 1/1980 | Jacklich | 604/224 |
| 4,277,238 | 7/1981 | Katagiri | 433/201 |
| 4,279,042 | 7/1981 | Andriacchi et al. . | |
| 4,284,080 | 8/1981 | Rehder | 128/305 |
| 4,302,855 | 12/1981 | Swanson . | |
| 4,304,178 | 12/1981 | Häberle | 100/93 P |
| 4,306,550 | 12/1981 | Forte | 128/92 |
| 4,337,773 | 7/1982 | Raftopoulos et al. | 128/305 |
| 4,341,206 | 7/1982 | Perrett et al. | 128/92 |
| 4,416,278 | 11/1983 | Miller | 128/305 |
| 4,466,429 | 8/1984 | Loscher et al. | 128/92 |
| 4,491,987 | 1/1985 | Park . | |
| 4,494,581 | 1/1985 | Gordon | 141/1 |
| 4,497,075 | 2/1985 | Niwa et al. | 3/1.9 |
| 4,502,159 | 3/1985 | Woodroff et al. | 3/1.4 |
| 4,516,276 | 5/1985 | Mittelmeier et al. | 3/1.91 |
| 4,520,511 | 6/1985 | Gianezio et al. . | |
| 4,523,587 | 6/1985 | Frey | 128/92 |
| 4,535,485 | 8/1985 | Ashman et al. | 623/16 |
| 4,552,136 | 11/1985 | Kenna | 128/92 |
| 4,561,432 | 12/1985 | Mazor | 128/92 |
| 4,576,152 | 3/1986 | Müller et al. | 128/92 R |
| 4,589,883 | 5/1986 | Kenna | 623/22 |
| 4,599,084 | 7/1986 | Nashef | 623/16 |
| 4,612,160 | 9/1986 | Donlevy et al. | 419/2 |
| 4,637,931 | 1/1987 | Schmitz | 424/78 |
| 4,642,124 | 2/1987 | Cooke | 623/23 |
| 4,644,942 | 2/1987 | Sump | 623/16 |
| 4,657,002 | 4/1987 | Ray | 128/92 |
| 4,657,549 | 4/1987 | Keller | 623/16 |
| 4,678,470 | 7/1987 | Nashef et al. | 623/16 |
| 4,678,471 | 7/1987 | Noble et al. | 623/16 |
| 4,686,972 | 8/1987 | Kurland | 128/92 |
| 4,705,032 | 11/1987 | Keller | 128/92 |
| 4,705,519 | 11/1987 | Hayes et al. | 623/16 |
| 4,706,659 | 11/1987 | Matthews et al. | 128/92 |
| 4,713,076 | 12/1987 | Draenert | 623/16 |
| 4,718,909 | 1/1988 | Brown | 623/16 |
| 4,728,335 | 3/1988 | Jurgutis | 623/23 |
| 4,751,922 | 6/1988 | DiPietropolo | 128/92 |
| 4,753,657 | 6/1988 | Lee et al. | 623/16 |
| 4,769,011 | 9/1988 | Swaniger | 604/218 |
| 4,777,942 | 10/1988 | Frey et al. | 128/92 |
| 4,795,467 | 1/1989 | Piez et al. | 623/16 |
| 4,800,875 | 1/1989 | Ray | 128/92 |
| 4,809,689 | 3/1989 | Anapliotis | 128/92 |
| 4,815,454 | 3/1989 | Dozier, Jr. | 128/92 |
| 4,846,161 | 7/1989 | Roger | 128/92 |
| 4,860,735 | 8/1989 | Davey et al. | 128/92 |
| 4,863,472 | 9/1989 | Törmälä | 623/16 |
| 4,865,608 | 9/1989 | Brooker, Jr. | 623/23 |
| 4,873,969 | 10/1989 | Huebsch | 128/92 |
| 4,877,020 | 10/1989 | Vieh | 128/92 |
| 4,881,536 | 11/1989 | Noble et al. | 606/94 |
| 4,888,023 | 12/1989 | Averill et al. | 623/22 |
| 4,896,662 | 1/1990 | Noble | 606/94 |
| 4,908,035 | 3/1990 | Deckner et al. | 623/23 |
| 4,919,153 | 4/1990 | Chin | 606/93 |
| 4,919,673 | 4/1990 | Willert et al. | 623/23 |
| 4,919,679 | 4/1990 | Averill et al. | 623/23 |
| 4,950,296 | 8/1990 | McIntyre | 623/16 |
| 4,986,826 | 1/1991 | Roger | 606/82 |
| 4,994,085 | 2/1991 | Sawai et al. | 623/23 |
| 5,015,256 | 5/1991 | Bruce et al. | 623/18 |
| 5,021,063 | 6/1991 | Täger | 623/23 |
| 5,047,033 | 9/1991 | Fallin | 606/87 |
| 5,047,035 | 9/1991 | Mikhail et al. | 606/93 |
| 5,049,151 | 9/1991 | Durham et al. | 606/98 |
| 5,078,746 | 1/1992 | Garner | 623/16 |
| 5,080,680 | 1/1992 | Mikhail et al. | 623/23 |
| 5,122,134 | 6/1992 | Borzone et al. | 606/80 |
| 5,152,763 | 10/1992 | Johnson | 606/86 |
| 5,171,288 | 12/1992 | Mikhail et al. | 623/23 |
| 5,192,283 | 3/1993 | Ling et al. | 606/93 |
| 5,192,300 | 3/1993 | Fowler | 606/213 |
| 5,269,785 | 12/1993 | Bonutti . | |
| 5,298,254 | 3/1994 | Prewett et al. | 424/422 |
| 5,329,846 | 7/1994 | Bonutti | 100/50 |
| 5,378,469 | 1/1995 | Kemp et al. | 424/423 |
| 5,385,566 | 1/1995 | Ullmark | 606/95 |
| 5,403,317 | 4/1995 | Bonutti . | |
| 5,470,336 | 11/1995 | Ling et al. | 606/105 |
| 5,507,813 | 4/1996 | Dowd et al. | 623/16 |
| 5,545,222 | 8/1996 | Bonutti . | |
| 5,577,517 | 11/1996 | Bonutti . | |
| 5,662,657 | 9/1997 | Carn | 606/95 |
| 5,665,121 | 9/1997 | Gie et al. | 623/16 |
| 6,019,765 | 2/2000 | Jacklich | 604/224 |

FOREIGN PATENT DOCUMENTS

| | | |
|---|---|---|
| 2658071 | 2/1990 | France . |
| 2662931 | 6/1990 | France . |
| 811018 | 6/1951 | Germany . |
| 2305441 | 8/1974 | Germany . |
| 2451275 | 5/1976 | Germany . |
| 2542056 | 3/1977 | Germany . |
| 3018491 | 11/1981 | Germany . |
| 3304476 | 9/1983 | Germany . |
| 3609122 | 8/1987 | Germany . |
| 3607823 | 9/1987 | Germany . |
| 3630069 | 1/1988 | Germany . |
| 1424829 | 9/1988 | Russian Federation . |
| 1409053 | 8/1975 | United Kingdom . |
| 1409054 | 8/1975 | United Kingdom . |
| 2069340 | 8/1981 | United Kingdom . |
| 2104391 | 3/1983 | United Kingdom . |
| 2153233 | 8/1985 | United Kingdom . |
| 2159129 | 11/1985 | United Kingdom . |
| 2162753 | 12/1986 | United Kingdom . |
| 8100670 | 3/1981 | WIPO . |
| 8602260 | 4/1986 | WIPO . |
| 8807355 | 10/1988 | WIPO . |
| WO 89/01322 | 2/1989 | WIPO . |
| 8904646 | 6/1989 | WIPO . |
| WO 93/01773 | 2/1993 | WIPO . |

OTHER PUBLICATIONS

Closed Intramedullary Bone–Grafting and Nailing of Segmental Defects of the Femur, Dr. Chapman; JBJS 1980.

A study of Autologous Cancellous Bone Particles in Long Bone Discontinuity Defects; Velasco et al., Jul./Aug. 1983.

Bone Graft Incorporation Around Titanium–Alloy–and Hydroxy Apatite–Coated Implants In Dogs; Soballe et al., Nov. 1991.

Bone Grafting and Noncemented Revision Arthroplasty of the Knee, K. Samuelson; Jan. 1988.

Revision Total Hip Arthroplasty With Titanium In-growth Prosthesis and Bone Grafting For Failed Cemented Femoral Component Loosening Gustilo et al., Oct. 1988.

The CPT Revision Hip Systems Surgical Technique, Zimmer, Inc. 1993.

CPT Hip System Brochure, Zimmer. Inc., 1994.

The CPT Hip System Surgical Technique, Zimmer, Inc., 1992.

Meeting Of The Hip Society and AAHKS, Clarion Plaza Hotel, Orlando, Florida, Feb. 19, 1995.

Excerpts from the Tumors, The Spine and Arthoplasty portions of Volume Two of Campbell's Operative Orthopaedics, Sixth Edition, published 1980.

Advanced Concepts in total Hip Replacement; Editor: William H. Harris, M.D., circa 1985.

Osteomill bone graft preparation device, Biodynamic Technologies, Inc., circa 1986.

FIG. 6A
FIG. 6B
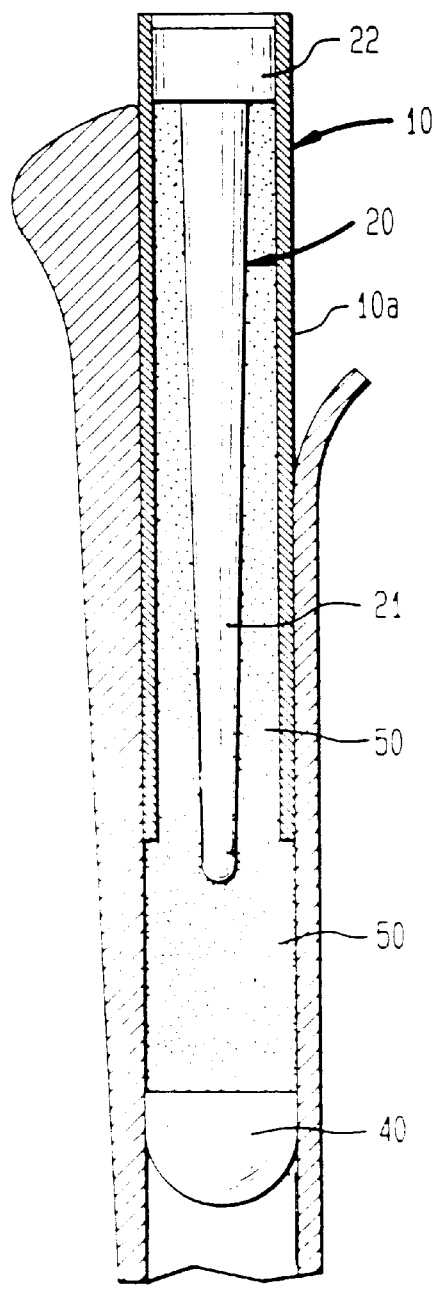
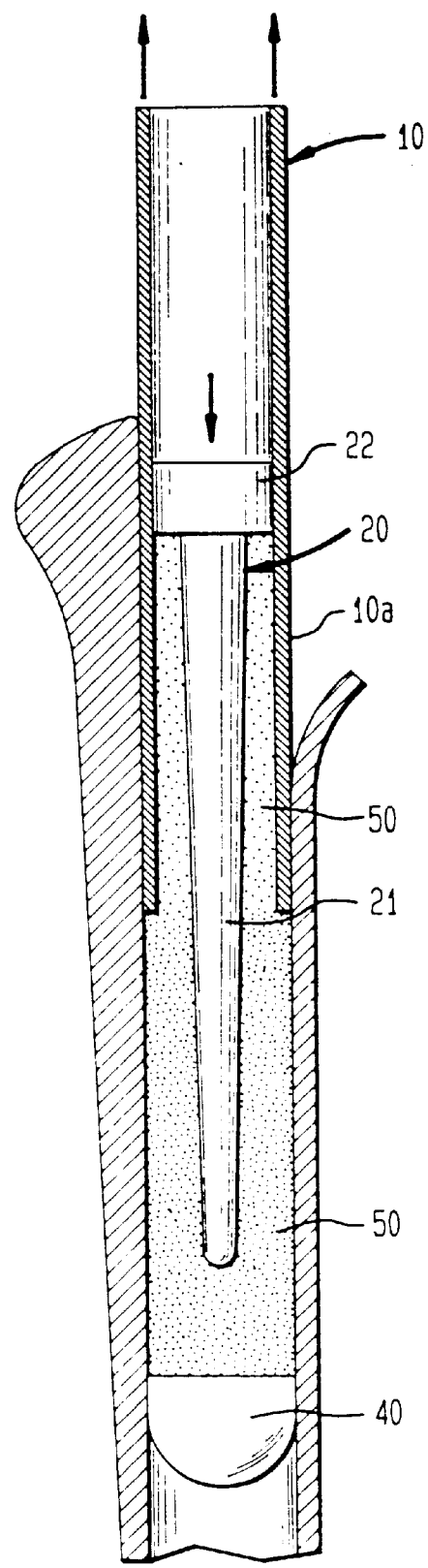

FIG. 6C
FIG. 6D
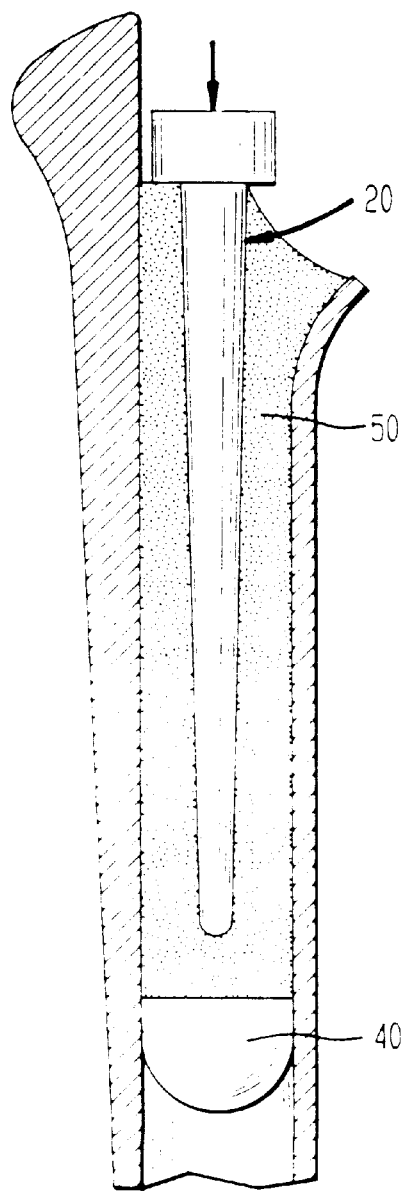
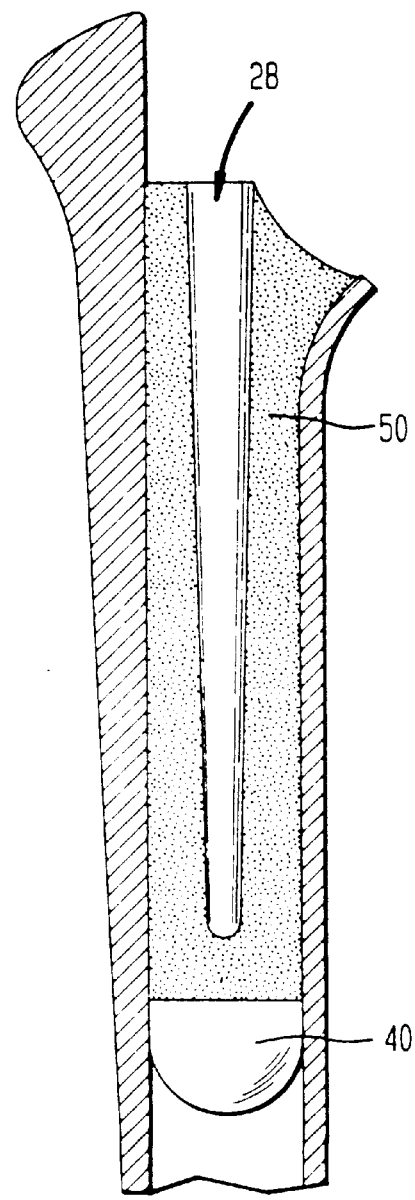

FIG. 7A
FIG. 7B
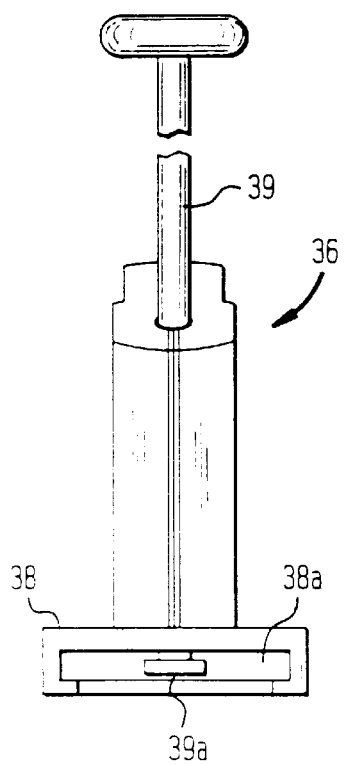
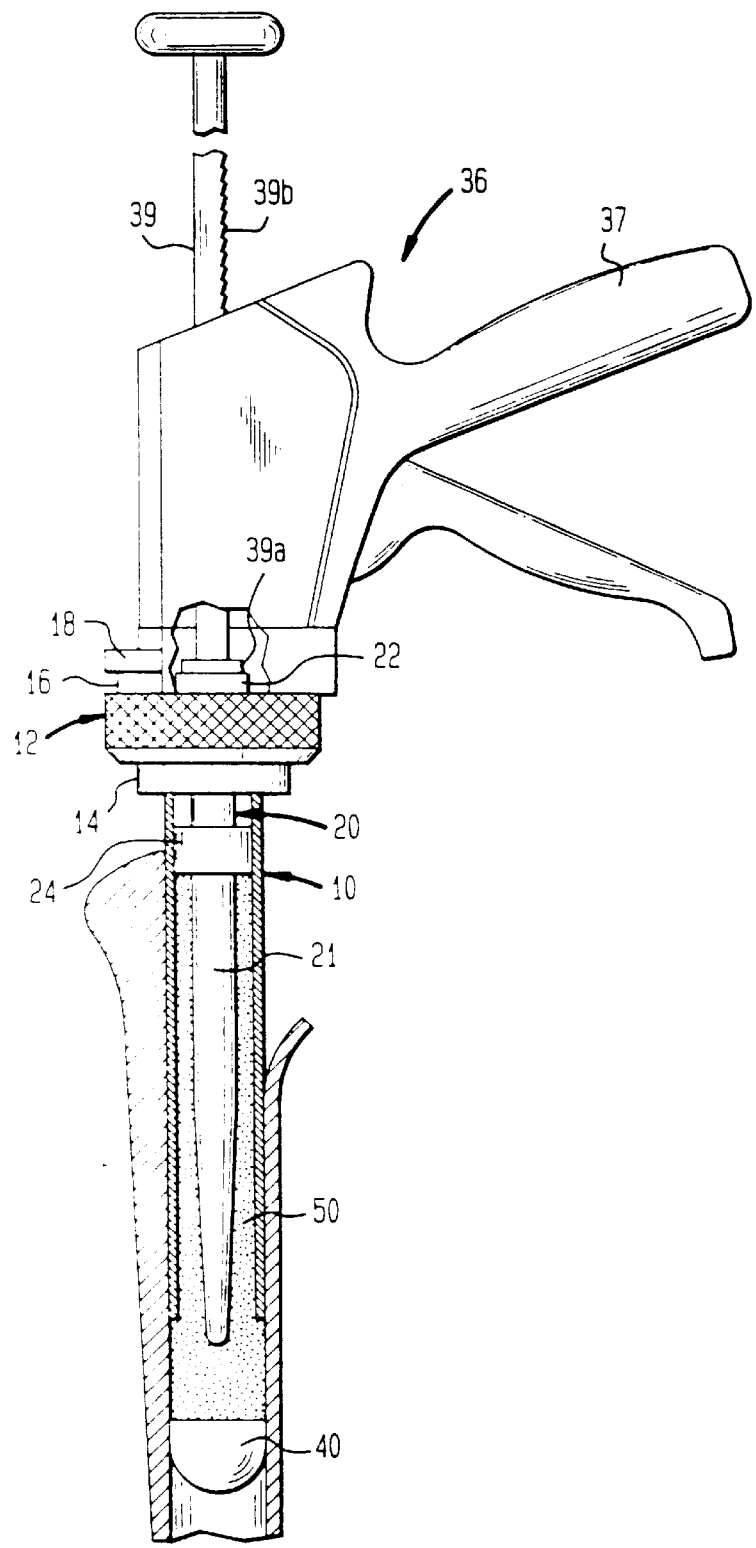

FIG. 8
FIG. 9
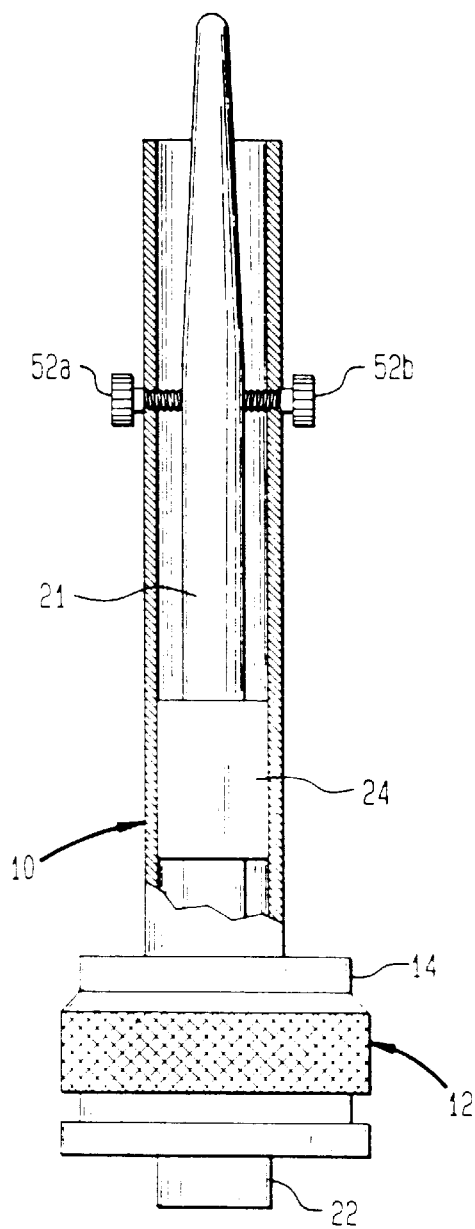
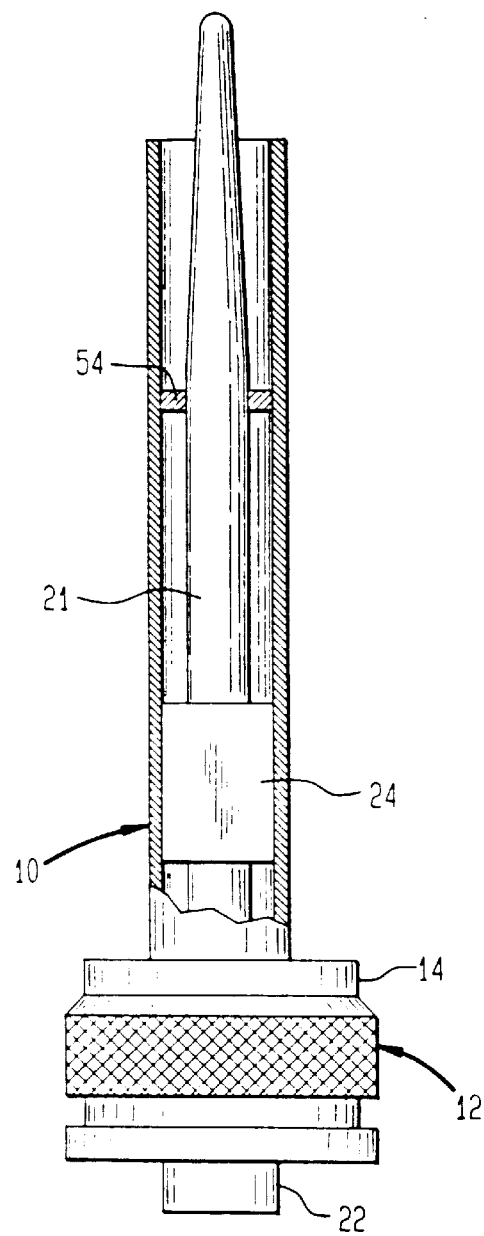

BONE GRAFT DELIVERY SURGICAL INSTRUMENTS

CROSS REFERENCE TO RELATED APPLICATIONS

This application is a divisional of U.S. patent application Ser. No. 08/988,095, filed Dec. 10, 1997, now U.S. Pat. No. 6,045,555, which is a continuation of U.S. patent application Ser. No. 08/336,841, filed Nov. 9, 1994, now U.S. Pat. No. 5,697,932, the disclosures of which are hereby incorporated by reference herein.

BACKGROUND OF THE INVENTION

The present invention relates generally to surgical instruments for implanting a new prosthesis at a joint, and for efficiently using bone graft to facilitate the implantation of a prosthesis.

It is known to use bone graft to prepare a seat for a prosthesis, either with or without a cement mantle. A bone grafting procedure is often used where there is an appreciable loss of strong bone stock, as is often the case in revision surgery (in which a previously implanted prosthesis is replaced with a new prosthesis). The seat prepared with bone graft may be made up entirely of bone graft to substantially surround a prosthesis, or the seat may be made up of bone graft and the natural bone at the implantation site (for instance, where bone graft is used to fill a relatively small void in the natural bone where the bone is otherwise intact). Bone graft typically includes crushed bone (cancellous and cortical), or a combination of these (and/or other natural materials) and synthetic biocompatible materials. Bone graft of this type is intended to stimulate growth of healthy bone. As used herein, "bone graft" shall mean materials made up entirely of natural materials, entirely of synthetic biocompatible materials, or any combination of these materials.

U.S. Pat. No. 5,015,256 to Bruce discloses a surgical technique by which the medullary canal is reamed and filled with bone graft, the bone graft being compacted by driving the stem of the prosthesis into the medullary canal. Also, U.S. Pat. No. 4,800,875 to Ray discloses a method of inserting bone graft into a bone and tamping the bone graft. European Patent Publication No. 0 179 626 A2 discloses the use of bone graft to enhance implant/bone contact, whereby the stem of a hip implant is intended to subside within an implant sleeve. Also, an article entitled "Histology Of Cancellous Impaction Grafting In The Femur," by Ling et al., Journal of Bone and Joint Surgery [Br], Vol. 75-B, No. Sep. 5, 1993, reports a 1988 revision of a hip implant in which allograft chips were impacted within the medullary canal with an oversized stem, followed by use of cement and implantation of a polished-surface stem. In addition, *Complications Of Total Hip Arthoplasty*, by Richard H. Rothman and William J. Hozack, W. B. Saunders Co., 1988, teaches a technique of bone grafting in the femoral canal in a revision surgery, using uncemented components.

Of course, it is desirable to properly prepare the medullary canal adjacent a joint for receiving bone graft so that a prosthesis can be properly positioned during implantation. Thus, the preparation of the medullary canal and the positioning of the prosthesis or trial prosthesis in the prepared medullary canal are often critical steps in properly implanting a prosthesis. To this end, rasps having a configuration similar to the prosthesis are well-known, as shown, for example, in U.S. Pat. No. 3,874,003 to Moser (FIG. 8), U.S. Pat. No. 4,306,550 to Forte and U.S. Pat. No. 4,552,136 to Kenna. These devices facilitate the proper shaping of the femoral medullary canal in a configuration which is similar to their respective hip prostheses or trial hip prostheses.

Centering devices (rods and guidewires) are also known for controlling the machining or other preparation of the medullary canal, as well as for centering a trial prosthesis during trial reduction or centering a prosthesis during implantation. U.S. Pat. No. 4,919,673 to Willert, U.S. Pat. No. 4,994,085 to Sawai and U.S. Pat. No. 5,078,746 to Garner each disclose the use of centering rods in the distal femoral canal to center hip joint prostheses and/or trial hip joint prostheses during trial reduction and final implantation. The hip joint prostheses and trial hip joint prostheses each have longitudinal passageways which receive the centering rods or guidewires already in the canal. Centering rods or guidewires are also used in connection with machining and shaping instruments so that the preparation of the canal is controlled about the centering rod or guidewire and so that the preparation is consistent from instrument to instrument. U.S. Pat. No. 4,341,206 to Perrett, U.S. Pat. No. 4,751,922 to DiPietropolo, U.S. Pat. No. 5,192,283 to Ling, U.S. Pat. No. 5,122,134 to Borzone and U.S. Pat. No. 5,190,548 to Davis disclose cannulated reamers and drills which are used with centering rods or guidewires for centering or positioning the shaping tools during preparation of a medullary canal or bone.

U.S. Pat. No. 5,192,283 to Ling also discloses the use of a trial hip prosthesis having a longitudinal passageway for receiving the very guidewire which facilitated the reaming and rasping of the canal. Bone graft is inserted into the canal around the guidewire, and the cannulated trial prosthesis is used to simultaneously compact and form or shape a prosthesis-receiving cavity larger than and similar in shape to the new prosthesis. Bone graft is continuously placed into the canal during the use of the cannulated trial prosthesis in order to build up the bone graft in the canal. A series of successively larger cannulated trial prostheses could be used to compact the bone graft.

The technique described in Ling is a somewhat time-consuming surgical procedure. Factors which add to the time-consuming nature of this technique include the steps which must be repeated to complete the insertion of bone graft into the canal and the requirement that all steps take place in the medullary canal. In addition, the technique described in Ling relies on a guidewire which could shift during preparation of the canal.

The present invention provides an easily implemented and efficient technique for the delivery of bone graft to a medullary canal or elsewhere in the body. One embodiment relates specifically to bone grafting within the medullary canal adjacent a joint to prepare the canal for receiving a prosthesis.

SUMMARY OF THE INVENTION

The present invention is directed to the delivery of bone graft materials to any area of the body and in particular to the medullary canal of any bone. The invention can be used in the repair of a bone or in connection with the implantation of prosthetic devices at any bone in the body, including without limitation the hip, knee and spinal joints. Further, the present invention can be used in primary surgery, in which a prosthesis is being used to reconstruct a joint for the first time, as well as in revision surgery, in which a previously-implanted prosthesis is being replaced with another prosthesis. Press fit, cement or other fixation techniques can be employed in conjunction with the present invention. The technique in accordance with the present invention is suitable for the delivery of bone graft into the medullary canal to fully or partially line the medullary canal.

One aspect of the present invention provides a bone graft delivery system for delivering bone graft, in a partially formed, fully formed or unformed condition to a graft receiving area in a body.

In a preferred embodiment, surgical instruments comprise a hollow tube constructed to receive bone graft, and a plunger adapted for insertion at least partially within the hollow tube. The plunger is constructed and arranged with respect to the hollow tube so as to form a positive impression in the bone graft when the bone graft and the plunger are within the hollow tube. The plunger is also constructed and arranged so that when the hollow tube is moved in a direction away from a graft receiving area, the bone graft is delivered to the graft receiving area with the same positive impression as that formed within the hollow tube.

In preferred embodiments, at least a portion of the positive impression formed in bone graft within the hollow tube is sized and shaped to receive at least a portion of a prosthesis. It is also preferred that the plunger includes an elongated rod portion. In preferred embodiments, the instruments include a graft retaining structure associated with the plunger and the hollow tube.

The instruments may include a tamp having a configuration which at least in part corresponds in shape to at least a portion of a prosthesis. The tamp may be adapted to further shape the positive impression in the bone graft after the bone graft is delivered to the graft receiving area.

In another aspect of the present invention, a kit of surgical instruments comprises a plurality of differently sized and/or shaped hollow tubes and a plurality of differently sized and/or shaped plungers. Each of the plungers correspond to at least one of the hollow tubes, whereby a surgeon may select a hollow tube and a plunger which correspond with one another depending upon the size and shape of the graft receiving area and the prosthesis to be implanted at such area. The corresponding hollow tubes and plungers are constructed and arranged such that bone graft can be placed within the hollow tube with the plunger, and the hollow tube can be moved away from a graft receiving area to leave the graft and plunger at such area.

The kit of surgical instruments preferably comprises a plurality of differently sized and/or shaped graft retaining structures, each corresponding to at least one hollow tube and at least one plunger.

The graft receiving area can be any area, but is often the medullary canal of a bone. In the preferred embodiment, the bone graft is delivered in a partially formed manner, and in accordance with another aspect of the present invention, requires further formation after initial delivery of the bone graft.

Another aspect of the present invention provides a method and apparatus by which a hollow tube and a plunger associated with the hollow tube are provided to facilitate delivery of the bone graft to a bone graft receiving area. In the preferred embodiment, positioning structure is provided on the plunger to maintain the plunger in a desirable position with respect to the hollow tube. Adjunct positioning means may also be provided to ensure that the plunger remains in the desirable position during the packing of bone graft into the hollow tube.

Another aspect of the present invention provides a method and apparatus by which a plunger and hollow tube assembly can be packed with bone graft, and then together inserted into the medullary canal or adjacent to another bone graft receiving area. Subsequently, the hollow tube can be withdrawn to leave the plunger in place in order to form in the bone graft a cavity in the shape of the plunger. In the preferred embodiment, the plunger can then be removed, and a series of sequentially larger trials can be used to shape the bone graft within the medullary canal.

Another aspect of the present invention provides a bone graft delivery system, by which bone graft can be selectively and controllably delivered to a specific area. For instance, bone graft may be delivered to one portion of the wall in the medullary canal, as opposed all of the walls in the medullary canal.

Another aspect of the present invention provides a hollow tube and plunger assembly, in which the hollow tube is disposable.

Another aspect of the present invention provides a bone graft delivery system, by which a hollow tube and possibly a hollow tube/plunger assembly can be prepared prior to even opening a patient, thus minimizing the overall impact of the grafting aspect of a surgical implantation or other procedure.

The present invention can be carried out by a method in which access is provided to a graft receiving area in a body, bone graft is placed into a hollow tube having a first end and a second end, the hollow tube, together with the bone graft, is arranged so that the first end of the hollow tube is at least adjacent to the graft receiving area, and the hollow tube is moved away from the graft receiving area, in a direction from the first end to the second end of the hollow tube, such that the bone graft exits the first end of the hollow tube and remains at the graft receiving area. A graft retaining structure may also be provided to block an end of the hollow tube, so as to facilitate the exit of the bone graft from the hollow tube. The graft retaining structure may also be used in such a way that it is maintained in one position while the tube is moved away from the graft receiving area. Alternatively, the graft retaining structure can be used by forcing it toward the graft receiving area, while the hollow tube is being moved away from the graft receiving area.

The present invention may also be carried out by exposing the medullary canal of a bone, placing bone graft into a hollow tube having a first end and a second end, inserting the first end of the hollow tube into the medullary canal, and withdrawing the hollow tube from the medullary canal, such that bone graft exits the first end of the hollow tube into the medullary canal. Again, the bone graft can be forced from the hollow tube by blocking an end of the hollow tube. The above technique may also include arranging a plunger having an elongate rod portion at least partially in the hollow tube and removing the plunger from the medullary canal to leave a cavity formed at least partially in the bone graft. The hollow tube can be inserted into the medullary canal together with the plunger and bone graft, and upon withdrawal of the hollow tube from the medullary canal, the plunger remains at least partially in the canal. Pressure can be applied to the plunger during withdrawal of the hollow tube to at least maintain the plunger at least partially in the medullary canal. Further pressure may also be applied to the plunger to force the plunger further into the medullary canal, either while withdrawing the hollow tube from the medullary canal or subsequent to the withdrawal of the hollow tube, whereby the bone graft deposited in the medullary canal would be further packed by the plunger.

The bone graft deposited in the medullary canal by the tube/plunger assembly can be shaped, if not already shaped, with a prosthesis or a trial prosthesis having a configuration similar to the prosthesis to be implanted. The bone graft material in the medullary canal can be compacted with successively larger trial prostheses to progressively shape the bone graft. If the prosthesis to be implanted is to be cemented in place in the canal, the final trial prosthesis used to shape the bone graft can be of a size larger than the prosthesis to be implanted, so as to leave a cement mantle.

The plunger used in connection with the hollow tube can be modular in nature, such that different portions of the plunger can be matched according to preoperative or intraoperative indications. Also, any positioning devices or graft retaining structures used in connection with the plunger can also be modular and selectable from a group of different devices to fit the particular application and hollow tube.

The present invention may also be carried out by providing a hollow tube having a first end and a second end, and being constructed so that it can receive bone graft, and so that the first end can be arranged at least adjacent to a bone graft receiving area, and so that bone graft can be delivered from the first end of the hollow tube to the bone graft receiving area upon movement of the hollow tube in a direction from the first end to the second end. A graft retaining structure can also be provided for use in connection with the hollow tube, as can a graft packer. In addition, a plunger can be provided with the hollow tube.

Another aspect of the present invention can be carried out by providing an extractor to facilitate the controlled movement of a tube which surrounds a rod, while leaving the rod substantially in position, the extractor including a housing, a connector for connecting the housing to the tube, a stem movable within the housing for applying pressure to a rod in its arranged position, and actuating means for applying pressure to such a rod. The stem may have a rod-engaging portion sized to engage a rod in a tube and to permit the tube to be withdrawn from around the rod so that the tube is disposed around the stem. The extractor is constructed and arranged so that upon actuation thereof, the stem applies pressure against the rod, and the housing, with a connected tube, is moved away from the arranged position, while leaving the rod in the arranged position.

BRIEF DESCRIPTION OF THE DRAWINGS

The foregoing and other objects of the present invention will become apparent, as will a better understanding of the concepts underlying the present invention, by reference to the description which follows and refers to the accompanying drawings in which:

FIGS. 6A–6F are elevational views, in partial cross-section of an implant technique in accordance with the present invention, illustrating in particular the delivery of bone graft to the proximal femoral medullary canal and the formation of the implant-receiving cavity within the graft-lined medullary canal;

FIG. 7A is a top plan view of a tube extractor (a modified cement injector) in accordance with the present invention;

FIG. 7B is an elevation view in partial cross-section of the bone graft delivery technique in accordance with the present invention, illustrating in particular the use of a tube extractor (associated with the extraction cap) to remove the hollow intramedullary tube from the medullary canal while leaving the plunger rod with the packed bone graft in place;

FIG. 8 is an elevational view of a plunger rod assembled within a hollow intramedullary tube, illustrating in particular adjunct centering means in the form of diametrically opposed centralizing screws;

FIG. 9 is an elevational view of a plunger rod assembled within a hollow intramedullary tube, illustrating in particular adjunct centering means in the form of a slideable centralizing washer held on the rod by an interference fit.

DETAILED DESCRIPTION OF THE INVENTION

FIGS. 1–4 illustrate some of the instruments which may be used to facilitate the delivery of bone graft in accordance with the present invention. The instruments illustrated are for the delivery of bone graft to the femoral medullary canal, but the concepts underlying the present surgical technique may be applied to the delivery of bone graft to the medullary canal of any bone, adjacent to or remote from any joint.

Figure 1:
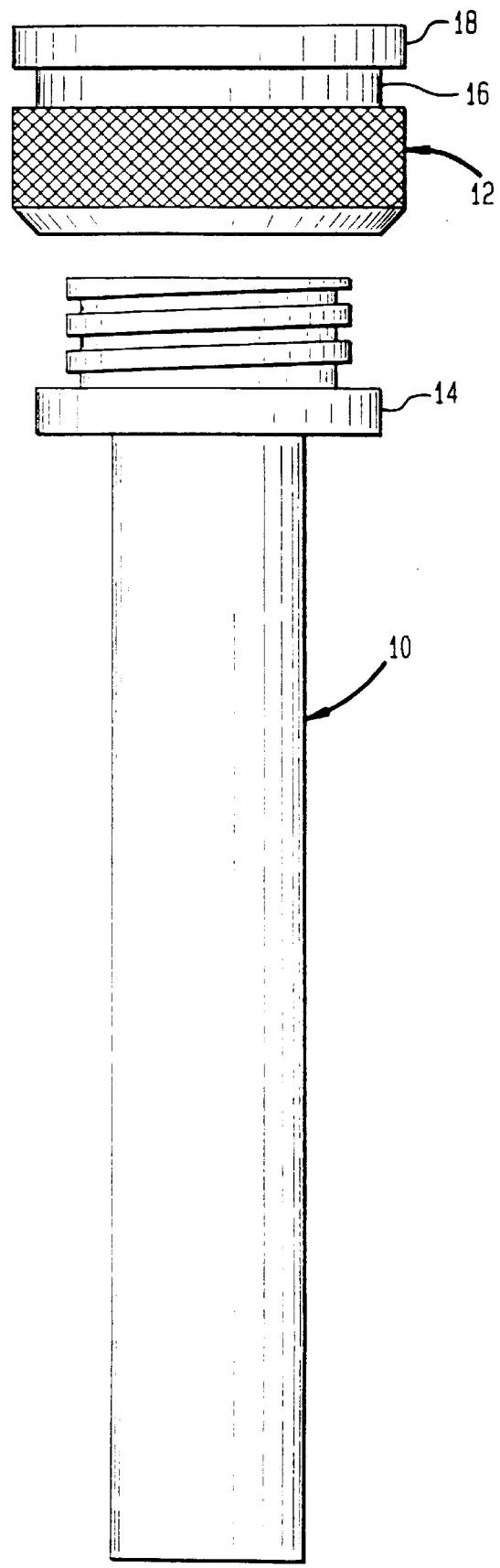
FIG. 1 is an elevational view of a hollow intramedullary tube and an associated extraction cap in accordance with an embodiment of the present invention.

FIG. 1 shows a hollow intramedullary tube 10 and an extraction cap 12 in accordance with the present invention. The tube is preferably hollow from one end to the other, but may be partially hollow depending upon the application and structure of the instruments used with it. (The word "hollow" will thus be used in this sense.) The tube 10 is preferably made of metal and preferably includes a thin-wall 10A (see FIG. 5) in at least the portion which will be inserted into a medullary canal. The tube 10 includes a tube flange 14 and male threads adapted to receive the female threads of the extraction cap 12 (see FIG. 5). The extraction cap 12 includes a groove 16 and retaining flange 18 for cooperation with the slotted retaining sleeve of a tube extractor (to be discussed later in connection with FIGS. 7A and 7B). The extraction cap 12 can be made of any suitable material, such as plastic or metal.

The hollow tube 10 and extraction cap 12 may also be made of a disposable material, such as a disposable plastic, so that these instruments can be disposed of after they are used once. If made of a disposable material, the extractor cap 12 can be made integrally with the hollow tube 10. Moreover, the hollow tube 10 can be made to be stored with bone graft in it for a period of time, whether the tube 10 is made of plastic, metal or any other material. In this regard, depending upon the surgical application, it may be desirable to only partially fill the tube for storage or at least not pack it tightly, so that a plunger can be inserted at the time of a surgery. The tube may also be made of a biocompatible material which can stay in the canal without impairing the final implantation. Alternatively, it may thus be a material that is resorbable, such as a resorbable polymer, in the canal after implantation, so as not to interfere with the growth of the bone or stability of the implant.

The hollow tube 10 can be of any suitable shape for insertion into the medullary canal of a bone (or any other area of the body) depending upon the application, but is preferably cylindrical in shape. In this regard, as used herein, "tube" shall be construed broadly to encompass structures of any suitable shape for retaining graft material prior to delivery to a medullary canal or any other area of the body. The tube 10 is preferably made in several different diameters, for example 16 mm, 18 mm, 20 mm and 22 mm. The selection of the appropriate tube 10 will depend upon preoperative and intraoperative indications. In this regard, the extraction cap 12 is preferably a "universal" extraction cap in the sense that only one extraction cap will be needed for an entire set of differently sized hollow intramedullary tubes. Thus, an instrument kit for a particular joint might include several differently-sized hollow intramedullary tubes to accommodate surgical needs.

As will be discussed in more detail below, reamers may be used to clean material (e.g., residual cement from previous implant, marrow, cancellous or cortical bone) out of the medullary canal prior to the insertion of the tube 10. An instrument kit might thus include a set of reamers corresponding in size to the hollow intramedullary tubes in that instrument kit. Once a medullary canal has been prepared with the appropriately sized reamer, the corresponding tube will properly fit in the canal.

Figure 2:
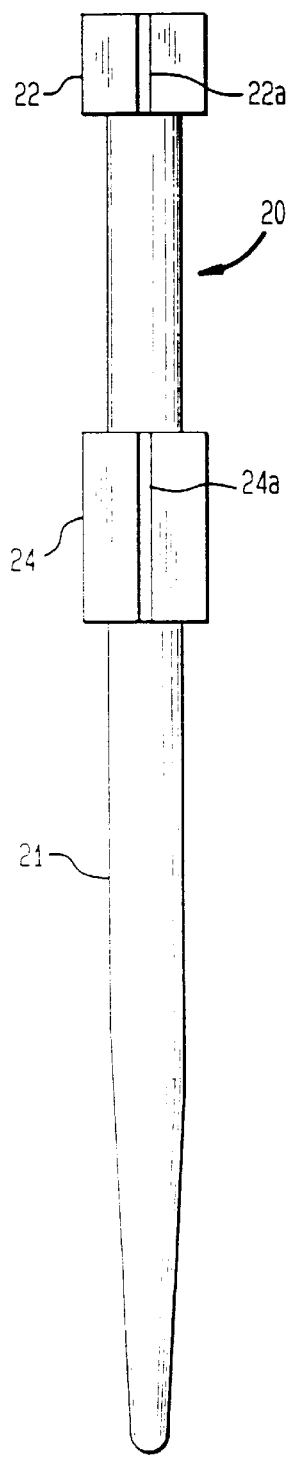
FIG. 2 is an elevational view of a plunger rod in accordance with an embodiment of the present invention.

FIG. 2 shows a plunger of an elongate construction having a centralizing cap or flange 22 at one end (the proximal end) and a centralizing collar 24. The centralizing cap 22 and the centralizing collar 24 are present to position—in this case, center—the plunger 20 within the tube 10. At least the centralizing collar 24 also serves a graft retaining function during the delivery of the bone graft to the medullary canal. This ensures that the bone graft is not withdrawn from the medullary canal as the tube 10 is being withdrawn from the canal. This may occur by maintaining the collar 24 in one position while withdrawing the tube 10, or by pushing it toward the bone graft exit of the tube to push bone graft out of the tube. The centralizing collar 24 may also facilitate the packing of the bone graft within the hollow tube 10 and within the medullary canal. In the tube 10, bone graft can be packed against the centralizing collar 24. In the medullary canal, after the tube 10 is withdrawn, additional bone graft may be placed into the proximal femoral medullary canal by the surgeon's fingers, and the plunger 20 can be used to facilitate the packing of the additional bone graft. By alternately lifting the plunger 20 out of the canal and inserting it back into the canal to impact the bone graft, the collar 24 further packs the additional bone graft in the proximal area.

Of course, various structures or devices could be used to center or otherwise position the plunger 20 or to ensure that the bone graft is transferred to the canal upon the withdrawal of the hollow tube 10. See, for example, the plunger shown in FIGS. 6A–6C and 10, which show positioning structures only at the proximal end of the plungers. However, the use of a centralizing cap 22 and a centralizing collar 24, separately situated, may be effective in reducing any toggle of the plunger 20 within the tube 10 and thus to maintain the plunger 20 within the desired position.

The centralizing cap 22 and the centralizing collar 24 include grooves 22a and 24a, respectively, for the release of air during the surgical procedure. This will facilitate the use of the plunger 20 while packing the tube/plunger assembly outside of the bone and while impacting the plunger 20 to further pack the bone graft material within the medullary canal.

The plunger 20 includes a rod portion 21 below the centralizing collar 24, which is to be inserted into the medullary canal. Rod portion 21 can be of any suitable size (length or thickness) and shape. In the preferred embodiment, the rod portion 21 is cylindrical in shape for more than half of the rod portion 21, the lower approximately one third being slightly tapered, as shown in FIG. 2. In fact, the rod portion 21 of the plunger 20 could emulate at least the distal portion of the implant stem which will finally be implanted in the canal, or it could emulate the entire stem of an implant. The degree of similarity between the rod portion 21 and the implant might depend on the joint being replaced, surgeon preference and other factors.

In the preferred embodiment, the centralizing cap 22 and collar 24 "bear" against the interior surface of the hollow tube 10 in that these structures were undersized with regard to the interior diameter of the hollow tube 10. Any tolerance between the outer diameter of a positioning device and the inner diameter of the hollow tube 10 that facilitates the desired positioning function (and graft retaining function, if desirable) is acceptable. However, free sliding movement of such a positioning or graft retaining device within the hollow tube is preferable. Of course, the above relates to the preferred embodiment of the present invention in which the positioning and/or graft retaining device is inside the hollow tube 10. Also, since the centralizing cap 22 and collar 24 in the preferred embodiment are sized to fit within the hollow tube 10, an instrument kit which includes several differently sized tubes 10 must also include a number of plungers 20 which correspond in size to the tubes 10.

Figure 3:
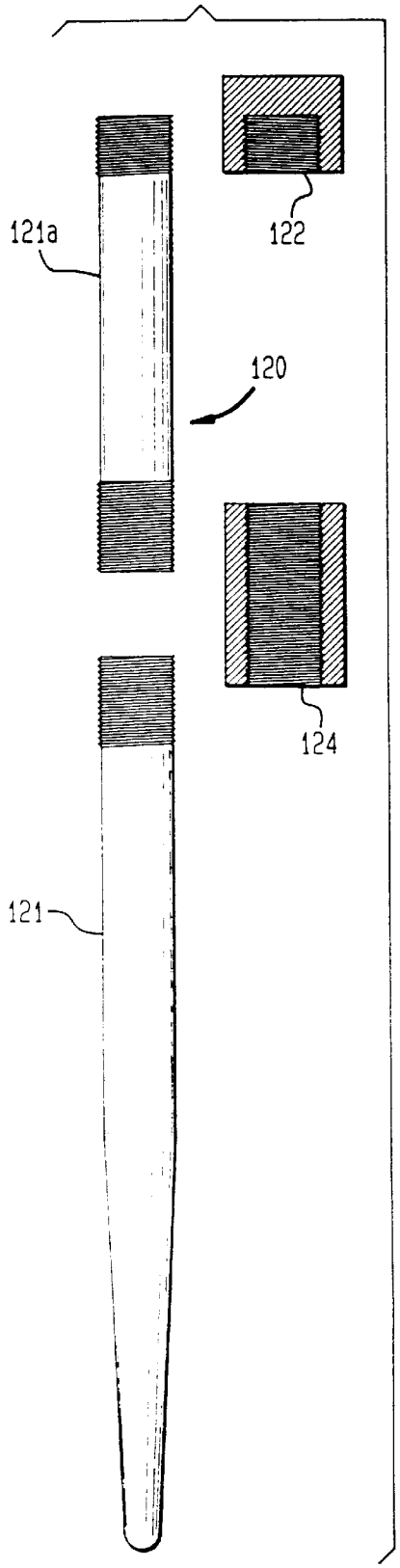
FIG. 3. is an elevational view of a modular plunger rod and associated modular centering devices, in accordance with another embodiment of the present invention.

FIG. 3 illustrates a modular plunger, generally designated as 120 and having a rod portion 121, which is separate from an upper portion 121a. (Alternatively, the rod portion 121 can be integral with the upper portion 121a to form yet a different modular plunger.) The rod portion 121 and upper portion 121a can be of different sizes, and an instrument kit may include several different sizes (widths and lengths) and shapes so that the rod portion 121 and upper portion 121a can be matched preoperatively or intraoperatively. The plunger 120 is adapted to receive, via a threaded connection or otherwise, any one of a plurality of centralizing caps 122 and centralizing collars 124. The centralizing caps 122 and centralizing collars 124 would be of different sizes to accommodate the differently sized tubes 10 within an instrument kit. Thus, one modular plunger 120 and several caps 122 and collars 124 would be required within a set of instruments. The appropriately sized centralizing caps 122 and centralizing collars 124 would be selected based on the selection of the tube 10. Of course, this type of modularity is not limited to centralizing caps and collars, but positioning devices of any type which might be used in connection with a plunger.

Figure 4:
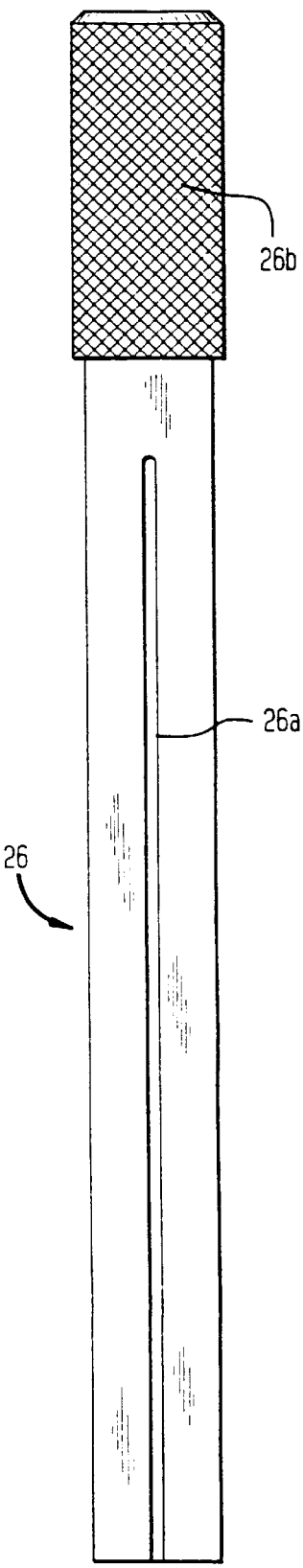
FIG. 4 is an elevational view of a hollow bone graft packer in accordance with the present invention.
Figure 5:
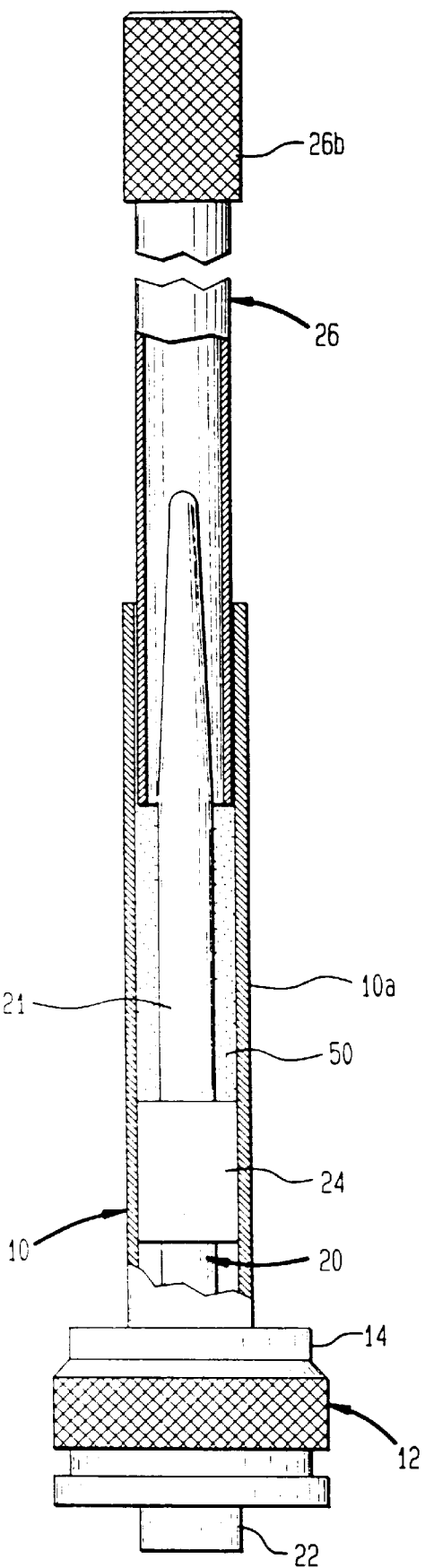
FIG. 5 is an elevational view of a plunger rod assembled within a hollow intramedullary tube (with extraction cap), illustrating in particular the packing of the tube/plunger assembly with bone graft through the use of a hollow bone graft packer.

FIG. 4 shows a hollow bone graft packer 26 which is adapted to be telescopically inserted into the hollow intramedullary tube 10 while the plunger 20 is in place within the hollow intramedullary tube 10. The bone graft packer 26 also includes grooves 26a for permitting air to escape during use, and further includes a knurled handle 26b at one end. As shown in FIG. 5, the bone graft packer 26 facilitates the packing of bone graft within the tube/plunger assembly. The bone graft packer 26 may also include a device (not shown) arranged at the packing end to enlarge the end of the packer 26 and thus facilitate packing. Such a device might be removably attached to the end of the packer 26, perhaps by threads. The device would provide a greater packing area to pack the bone graft in the donut-shaped area around the plunger 20 and within the tube 10.

As shown in FIG. 5, the bone graft material, generally designated as 50, is packed within the tube 10 by the bone graft packer 26 such that the bone graft material 50 surrounds the rod portion 21 of plunger 20. Here, the bone graft material 50 is preferably packed as tightly as possible within the tube 10. The initial packing step may include inverting the tube/plunger assembly and pushing it into a container of bone graft to begin filling the tube with bone graft.

While FIG. 5 illustrates the packing of the bone graft within the tube 10 while the plunger 20 is within the tube 10, the tube 10 could be partially or fully packed prior to insertion of the plunger 20. Once the plunger 20 is inserted into the tube 10, further compaction of the bone graft material 50 could be accomplished through the use of the bone graft packer 26.

FIGS. 6A–6F illustrate the delivery of the bone graft material 50 to the femoral medullary canal in accordance with an embodiment of the present invention. However, prior to the steps shown in FIG. 6A, the tube/plunger assembly must be prepared (e.g., as described above with respect to FIG. 5), and the medullary canal of the distal femur must be prepared. A particular advantage of the preferred embodiment of the present invention resides in the fact that the tube/plunger assembly can be packed and prepared for use prior to even exposing the patient's bone.

The preparation of the distal femoral medullary canal may include the revision or removal of a previously implanted hip implant, distal plug (if any) and any associated cements or other materials. An appropriately sized reamer, selected preoperatively and/or intraoperatively, may be used (if necessary) to clean the medullary canal to a size corresponding to the selected hollow intramedullary tube 10. The material cleaned out may include cement, marrow and/or bone, depending upon surgeon preference, the application, etc. A distal plug 40 may then be inserted into the medullary canal at a location which is selected preoperatively and/or intraoperatively. The next preferable step in the bone graft delivery technique in accordance with the present invention is to pack an appropriate amount, e.g., 1–2 inches, of bone graft material 50 against the distal plug 40 (which can be of any suitable material or structure). This can be accomplished with any suitable instrument which fits into the medullary canal. The medullary canal is now prepared for receiving the tube/plunger assembly.

As shown in FIG. 6A, the tube/plunger assembly is inserted into the prepared femoral medullary canal against the distal plug 40 and/or any bone graft material which was previously packed against the distal plug 40. It is noted that the plunger 20 illustrated in FIG. 6A has a rod portion 21 which is conical in shape as opposed to cylindrical with a distal taper (as in FIGS. 2 & 3). Also, the plunger 20 in FIG. 6A includes a cap or thin flange 22 at its proximal end to facilitate the positioning, in this case centering, of the plunger 20 within the tube 10.

FIG. 6B illustrates the delivery of the bone graft material 50 to the medullary canal by reason of the withdrawal of the tube 10 from the medullary canal, simultaneously with the application of pressure, from the proximal towards the distal end, of the plunger 20. The plunger 20 may be held in one place (by such pressure) while the tube 10 is being withdrawn from the medullary canal, or further pressure can be applied to push the plunger 20 into the medullary canal at the same time the tube 10 is being withdrawn. Pressure can be applied against the plunger 20 by the rod 39 of the extractor 36 (shown in FIG. 7B and described below), or with a rod driver (not shown), which may be held against the plunger 20 by the surgeon while withdrawing the tube 10. In some cases, there may be some incidental proximal movement of the plunger, but this is not preferable (even though the application of further pressure to the plunger will move the plunger into the desired position).

During withdrawal of the tube 10, the centralizing collar 24 (shown in FIG. 2) prevents at least any appreciable amount of bone graft 50 from moving out of the canal with the tube 10, and forces the bone graft 50 distally so that it is transferred into the canal. As the tube 10 is withdrawn from the medullary canal, the space occupied by its thin walls 10A is filled with the bone graft material 50. Preferably, it is then packed more tightly by the plunger 20.

Following the withdrawal of the tube 10, the plunger 20 is preferably forced further into the medullary canal to further compact the bone graft material 50. This can be accomplished in any suitable manner, including the impaction of the top of the plunger 20. FIG. 6C shows the further compaction of the bone graft material. Once the desired degree of bone graft compaction has been attained, the plunger 20 is removed from the medullary canal. The length of the plunger 20 between the centralizing collar 24 and cap 22, and the cap 22 itself, facilitate the removal of the plunger 20. This leaves a plunger cavity 28 within the packed bone graft material, as shown in FIG. 6D.

Figure 6E:
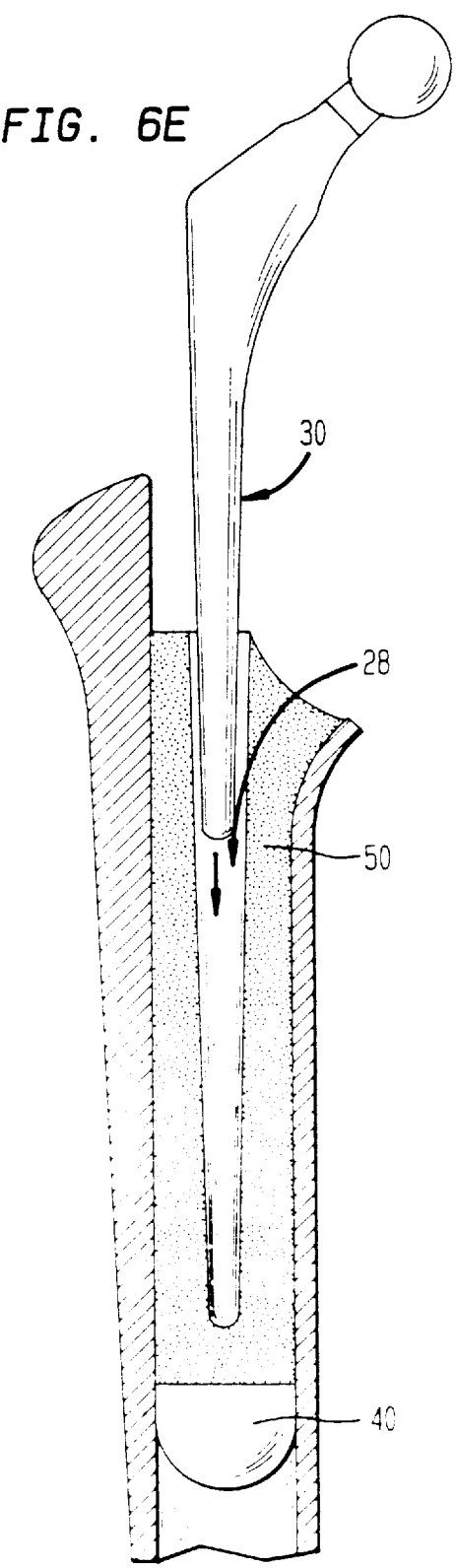

The medullary canal is now prepared for trial packing and reduction. Preferably, the packing is accomplished through the sequential use of a set of trial implants, ranging from small to larger. As is well known in the field, trial implants often have a shape which is the same or similar to the final implant. FIG. 6E shows a trial hip implant 30, which represents any trial of a set of differently sized trial hip implants. While the bone graft 50 has been well compacted through the use of the plunger 20, trial implant 30 and subsequent trial implants are used within the plunger cavity 28 to shape the bone graft 50 and thus form a cavity which matches the final implant, as shown in FIG. 6E. The sequential use of successively larger trial implants facilitates the efficient shaping of the bone graft 50. The last trial implant used may match the size, as well as the shape, of the final implant, or if the final implant is to be cemented, the last trial implant used may be of a size larger than the size of the final implant. This will leave sufficient room for a cement mantle 32 within the cavity formed in the bone graft 50. During the use of the trial implants 30 to shape the plunger cavity 28, it is preferable to finger-pack or otherwise pack bone graft 50 in the proximal area of the femoral medullary canal so that the shape of the proximal portion of the trial implant 30, and thus the final implant 35, is adequately formed in the canal.

Figure 6F:
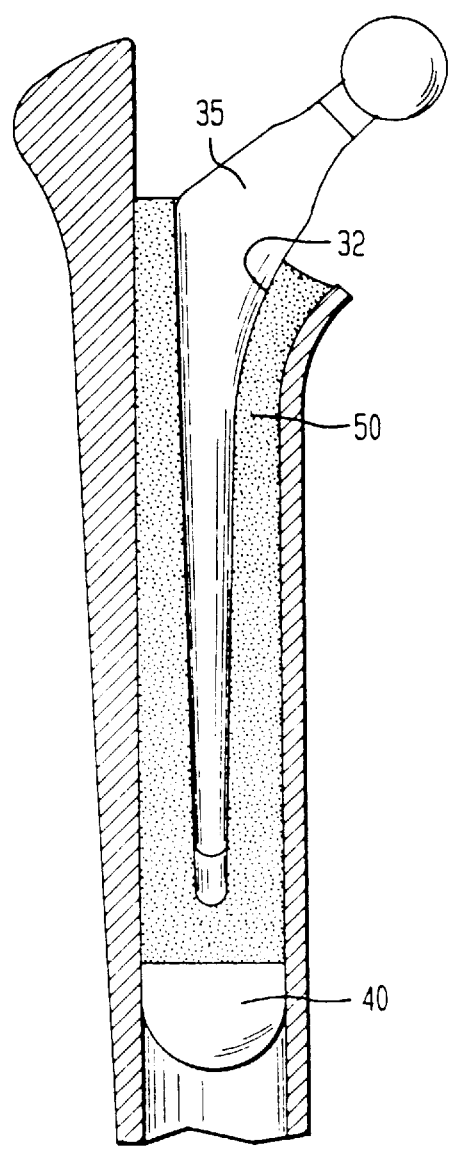

FIG. 6F shows the implantation of the final implant 35. As is shown in FIG. 6F, a cement mantle space 32 is provided between the bone graft 50 and the implant 35.

The present invention relates not only to the delivery of bone graft material to the medullary canal of a bone, but also relates to the delivery of bone graft material to any portion of a bone which requires bone graft material. Thus, for example, the technique contemplates delivery to a window cut in a bone, where access to such window for bone grafting is difficult to obtain because of muscle tissue, etc. In other words, the window in the bone may not be fully exposed, such that the hollow tube may be helpful in selectively and controllably placing bone graft material in or adjacent to such window. The present invention also contemplates the delivery of bone graft material with or without the use of a plunger to form a cavity in delivered bone graft material. Thus, the bone graft material can simply be delivered to an area via the hollow tube and without the plunger.

FIG. 7A shows a tube extractor 36, which is quite similar to a caulk gun used to dispel adhesive from an adhesive tube. Specifically, for purposes of this invention, modifications were made to a cement injector sold by Stryker Corporation of Kalamazoo, Mich. under catalog #206-600. The modified cement injector or tube extractor 36 can be used to facilitate the withdrawal of the tube 10 during the delivery of the bone graft 50 into the medullary canal. The tube extractor 36 includes a slotted retaining sleeve 38 which has a slot 38A for receiving the retaining flange 18 of the extraction cap 12 (shown in FIG. 7B), thereby connecting the extractor 36 to the extraction cap 12 and thus the tube 10. The slot 38A and the slotted retaining sleeve 38 have been in other instances used to hold the flange of a container of cement or other material. The extractor 36 includes a rod 39 and a rod collar 39a which will bear against the centralizing cap 22 or other structure at the end of the plunger 20. This is shown in the cutaway portion in FIG. 7B. As with many caulk guns, the rod 39 includes ratchet teeth 39b which facilitate the advancement of the rod 39 when the extractor handle 37 is actuated. However, any other suitable means for advancing the rod 39 can be used.

FIG. 7B shows the extractor 36 connected to the extraction cap 12 via the slotted retaining sleeve 38 of the extractor 36 and the groove 16 and retaining flange 18 of the extraction cap 12. In FIG. 7B, the extraction cap 12 is connected to the tube 10 against the tube flange 14. The plunger 20 is assembled within the tube 10 and is surrounded by the bone graft 50. The rod collar 39a is shown in the cut-away portion bearing against the centralizing cap 22.

In practice, upon the actuation of the extractor handle 37, the rod 39 of extractor 36 will be forced downwardly against the plunger 20. Because the plunger 20 is bearing against either the distal plug 40 or compacted bone graft 50 which is against the distal plug 40, the tube 10 will move distally out of the medullary canal, leaving the plunger 20 in place (or forcing it further downwardly). While the tube 10 can be withdrawn in any suitable manner, the use of the extractor 36 may be quite helpful in controllably removing the tube 10.

While centralizing cap 22 and collar 24 serve the purpose, among others, of centralizing the rod portion 21 of plunger 20 during initial assembly of the tube 10 and plunger 20, it is possible that the centralized position might be moved after that initial assembly. This may occur during the insertion and packing of the bone graft material 50 around the rod portion 21 within the tube 10. To ensure that the packing of the bone graft material 50 within the tube/plunger assembly does not shift the rod portion 21 from its centralized position, adjunct centralizing means can be employed. FIG. 8 illustrates the use of two centralizing screws 52a and 52b, which threadedly engage diametrically opposed holes in the tube 10 and engage the rod portion 21. Together these centralizing screws help ensure that the rod portion 21 remains in the centralized position. The structure of these centralizing screws 52a and 52b may be changed to accommodate any position (other than central) of the rod portion 21 within the tube 10. In addition, while the centralizing screws 52a and 52b are disclosed as adjunct positioning means, they can be used (as shown or in additional pairs) as primary positioning means in lieu of cap 22 and collar 24, or just in lieu of collar 24 (so that they would work with cap 22).

FIG. 9 illustrates yet another technique for ensuring that the rod portion 21 remain in the centralized position (or any other desirable position). Here, a centralizing washer 54 (or multiple such washers) may be used. This washer 54, preferably made out of a plastic material, is inserted over the rod portion 21, and remains in place by an interference fit. In the preferred embodiment of these washers, radial relief cuts are made from the central hole, so that the washer can be slid over a tapering rod. Thus, the washer 54 can be further forced onto the cylindrical portion of the rod portion 21 during the packing of the tube/plunger assembly. The washer 54 will finally rest against the centralizing collar 24, but in the meantime will have helped ensure that the position of the rod portion 21 remains as it was originally set. The possibility of the washer 54 being left behind after removal of the tube 10 and the plunger 20 has been recognized. Thus, the washer 54 is preferably biocompatible and detectable by X-ray. It might be such that the washer 54 can be left in place with no harm to the subsequent implantation, or the washer 54 can be extracted prior to finally preparing the canal. As with the centralizing screws 52a and 52b, the washer 54 or multiple washers may be useable as the primary positioning means, alone or with one or both of cap 22 or collar 24.

Figure 10:
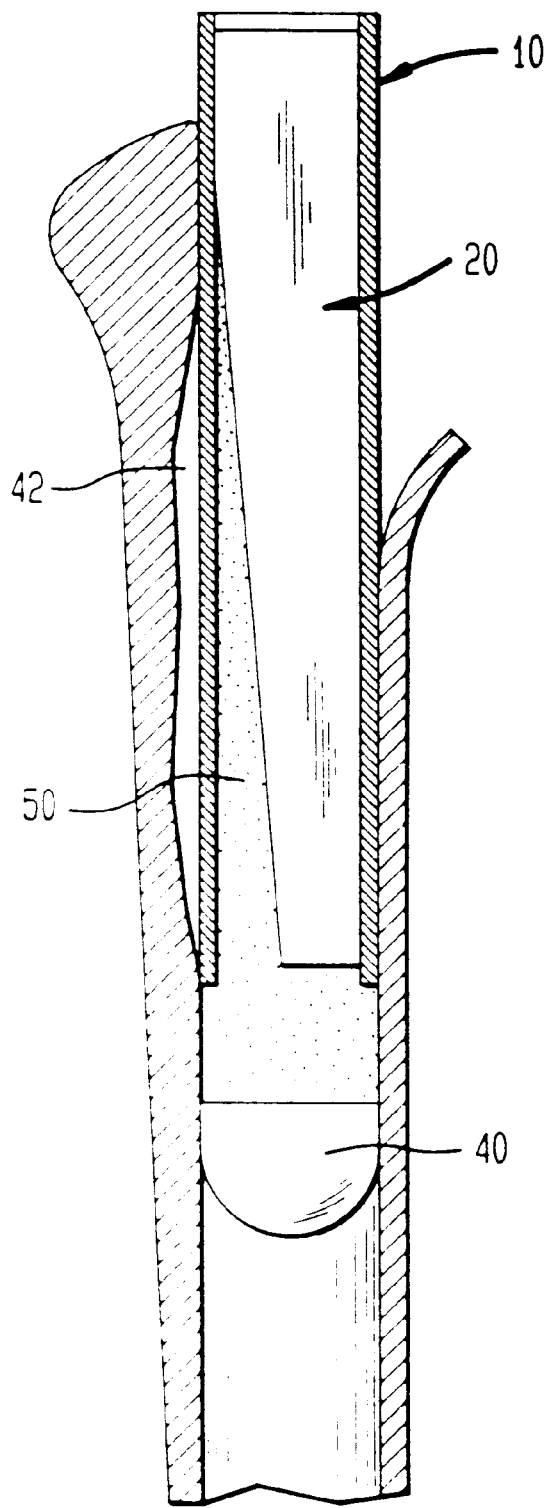
FIG. 10 is an elevational view, in partial cross-section, showing the selective delivery of bone graft to a specific area of the medullary canal through the use of a specifically structured plunger rod.

FIG. 10 illustrates a particular specialized application using the present invention. In FIG. 10, the distal femoral bone includes a void 42 on the lateral side of the medullary canal. In this particular application, it may be desirable to clean only the area which has been damaged, while maintaining the strong bone stock in other areas of the medullary canal. Thus, the objective is to selectively place bone graft 50 only in void 42. Once the selected area has been cleaned, the selective delivery of bone graft can be accomplished through the use of a tube 10 and a plunger 20, wherein the plunger 20 has a particular shape and/or orientation with regard to the tube 10 to facilitate selective delivery of the bone graft 50 to the void 42. One way of accomplishing this is shown in FIG. 10. In FIG. 10, the bone graft 50 is only provided on the lateral side of the plunger 20. It is also noted that the plunger 20 includes flattened areas at least at the top of proximal portion to facilitate the positioning of the plunger 20 within the tube 10. Upon withdrawal of the tube 10, and the further compaction of the bone graft 50, the void 42 is filled or at least partially filled with the bone graft 50. A further procedure, such as implantation of a prosthetic device, can now be undertaken.

While the foregoing description of figures illustrate the preferred embodiments of the bone graft delivery technique and associated instruments in accordance with the present invention, it should be appreciated that certain modifications can be made and are encouraged to be made without departing from the spirit and scope of the present invention which is intended to be captured by the claims set forth immediately below.

What is claimed is:

1. Surgical instruments comprising a hollow tube constructed to receive bone graft, and a plunger adapted for insertion at least partially within said hollow tube, whereby the plunger is constructed and arranged with respect to the hollow tube so as to form a positive impression in the bone graft when the bone graft and the plunger are within said hollow tube, and the plunger is further constructed and arranged so that when the hollow tube is moved in a direction away from a graft receiving area, the bone graft is delivered to the graft receiving area with the same positive impression as that formed within the hollow tube.

2. The instruments in claim 1, further including a tamp having a configuration which at least in part corresponds in shape to at least a portion of a prosthesis, the tamp being adapted to further shape the positive impression in the bone graft after the bone graft is delivered to the graft receiving area.

3. The instruments in claim 1, wherein at least a portion of the positive impression formed in bone graft within the hollow tube is sized and shaped to receive at least a portion of a prosthesis.

4. The instruments in claim 1, wherein said plunger includes an elongated rod portion.

5. The instruments in claim 4, further including a graft retaining structure associated with said plunger and said hollow tube.

* * * * *